(12) United States Patent
Ostrovsky et al.

(10) Patent No.: US 9,462,932 B2
(45) Date of Patent: Oct. 11, 2016

(54) STRUCTURE FOR USE AS PART OF A MEDICAL DEVICE

(75) Inventors: Isaac Ostrovsky, Wellesley, MA (US); Ty Fairneny, Hopkinton, MA (US); Josef Slanda, Milford, MA (US); Jessica Hixon, Watertown, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 958 days.

(21) Appl. No.: 12/358,624

(22) Filed: Jan. 23, 2009

(65) Prior Publication Data
US 2009/0192495 A1    Jul. 30, 2009

Related U.S. Application Data

(60) Provisional application No. 61/023,235, filed on Jan. 24, 2008.

(51) Int. Cl.
*A61M 25/00* (2006.01)
*A61B 1/005* (2006.01)
*A61M 25/01* (2006.01)

(52) U.S. Cl.
CPC ........... *A61B 1/0055* (2013.01); *A61B 1/0057* (2013.01); *A61M 25/0138* (2013.01); *A61M 25/0147* (2013.01); *A61M 2025/0059* (2013.01); *A61M 2025/0161* (2013.01)

(58) Field of Classification Search
CPC ................. A61M 2025/015; A61M 25/0138; A61M 25/0147; A61M 25/0105; A61M 25/0133; A61B 1/0055; A61B 1/0051; A61B 1/0057
USPC ....................................................... 600/585
See application file for complete search history.

(56) References Cited

U.S. PATENT DOCUMENTS 3,924,632 A    12/1975   Cook
4,203,430 A     5/1980   Takahashi
(Continued)

FOREIGN PATENT DOCUMENTS

DE     100 52 679 A1    5/2001
EP      0 422 887 A2    4/1991
(Continued)

OTHER PUBLICATIONS

Notification of Transmittal of the International Search Report and the Written Opinion of the International Searching Authority, or the Declaration. Issued in corresponding international application No. PCT/US2009/031789, mailed May 8, 2009.
(Continued)

*Primary Examiner* — Lee S Cohen
*Assistant Examiner* — Emily Lloyd
(74) *Attorney, Agent, or Firm* — Bookoff McAndrews, PLLC (57) ABSTRACT

The present invention generally relates to an articulating structure for use as at least part of a medical device. In one aspect, the invention features an articulating structure comprising an inner member, a sleeve, a pull wire, and an outer member. The inner member defines at least one channel on the outer surface of the inner member, the at least one channel extending along a length of the inner member. The inner member further defines at least one lumen extending through the inner member. The sleeve is disposed in the at least one channel. The pull wire extends within a lumen of the sleeve. The outer member is disposed over the inner member and defines a lumen through which the inner member extends.

20 Claims, 6 Drawing Sheets

(56) References Cited

U.S. PATENT DOCUMENTS

| | | | |
|---|---|---|---|
| 4,425,919 A | 1/1984 | Alston, Jr. et al. | |
| 4,430,083 A | 2/1984 | Ganz et al. | |
| 4,456,761 A | 6/1984 | Krapcho | |
| 4,546,761 A | 10/1985 | McCullough | |
| 4,806,182 A | 2/1989 | Rydell et al. | |
| 4,852,565 A | 8/1989 | Eisele | |
| 4,911,148 A | 3/1990 | Sosnowski et al. | |
| 5,005,558 A | 4/1991 | Aomori | |
| 5,037,404 A | 8/1991 | Gold et al. | |
| 5,168,864 A * | 12/1992 | Shockey | 600/146 |
| 5,271,382 A | 12/1993 | Chikama | |
| 5,313,967 A | 5/1994 | Lieber et al. | |
| 5,381,782 A | 1/1995 | DeLaRama et al. | |
| 5,477,856 A | 12/1995 | Lundquist | |
| 5,480,382 A | 1/1996 | Hammerslag et al. | |
| 5,562,619 A | 10/1996 | Mirarchi et al. | |
| 5,662,119 A | 9/1997 | Brennen et al. | |
| 5,702,754 A | 12/1997 | Zhong | |
| 5,706,826 A | 1/1998 | Schwager | |
| 5,795,341 A | 8/1998 | Samson | |
| 5,857,964 A | 1/1999 | Konstorum et al. | |
| 5,865,800 A | 2/1999 | Mirarchi et al. | |
| 5,873,817 A | 2/1999 | Kokish et al. | |
| 5,938,588 A | 8/1999 | Grabover et al. | |
| 6,012,494 A | 1/2000 | Balazs | |
| 6,048,620 A | 4/2000 | Zhong | |
| 6,068,623 A | 5/2000 | Zadno-Azizi et al. | |
| 6,123,699 A * | 9/2000 | Webster, Jr. | 604/528 |
| 6,171,235 B1 | 1/2001 | Konstorum et al. | |
| 6,224,587 B1 | 5/2001 | Gibson | |
| 6,240,231 B1 | 5/2001 | Ferrera et al. | |
| 6,352,531 B1 | 3/2002 | O'Connor et al. | |
| 6,352,539 B1 | 3/2002 | Avellanet | |
| 6,450,948 B1 | 9/2002 | Matsuura et al. | |
| 6,475,140 B1 | 11/2002 | Konstorum et al. | |
| 6,485,411 B1 | 11/2002 | Konstorum et al. | |
| 6,572,535 B2 | 6/2003 | Watanabe et al. | |
| 6,589,227 B2 | 7/2003 | Sønderskov Klint | |
| 6,656,195 B2 | 12/2003 | Peters et al. | |
| 6,740,030 B2 | 5/2004 | Martone et al. | |
| 6,749,560 B1 | 6/2004 | Konstorum et al. | |
| 6,780,151 B2 | 8/2004 | Grabover et al. | |
| 6,783,510 B1 | 8/2004 | Gibson et al. | |
| 6,790,173 B2 | 9/2004 | Saadat et al. | |
| 6,817,974 B2 | 11/2004 | Cooper et al. | |
| 6,858,005 B2 | 2/2005 | Ohline et al. | |
| 6,890,329 B2 | 5/2005 | Carroll et al. | |
| 6,907,298 B2 | 6/2005 | Smits et al. | |
| 6,916,285 B2 | 7/2005 | Takase | |
| 6,942,659 B2 | 9/2005 | Lehmann et al. | |
| 6,991,616 B2 | 1/2006 | Bencini et al. | |
| 7,011,655 B2 | 3/2006 | Thompson et al. | |
| 7,037,290 B2 | 5/2006 | Gardeski et al. | |
| 7,048,717 B1 | 5/2006 | Frassica | |
| 7,070,608 B2 | 7/2006 | Kurz et al. | |
| 7,089,063 B2 | 8/2006 | Lesh et al. | |
| 7,090,637 B2 | 8/2006 | Danitz et al. | |
| 7,090,683 B2 | 8/2006 | Brock et al. | |
| 7,101,361 B2 | 9/2006 | Gardeski | |
| 7,105,000 B2 | 9/2006 | McBrayer | |
| 7,182,764 B2 | 2/2007 | Jenkins et al. | |
| 2003/0009095 A1 | 1/2003 | Skarda | |
| 2003/0130712 A1 | 7/2003 | Smits et al. | |
| 2004/0186350 A1 | 9/2004 | Brenneman et al. | |
| 2004/0199052 A1 | 10/2004 | Banik et al. | |
| 2004/0225186 A1 | 11/2004 | Horne, Jr. et al. | |
| 2004/0236316 A1 | 11/2004 | Danitz et al. | |
| 2005/0015072 A1 | 1/2005 | Engel et al. | |
| 2005/0054951 A1 | 3/2005 | Parins | |
| 2005/0075661 A1 | 4/2005 | Levine et al. | |
| 2005/0090809 A1 | 4/2005 | Cooper et al. | |
| 2005/0096694 A1 | 5/2005 | Lee | |
| 2005/0107667 A1 | 5/2005 | Danitz et al. | |
| 2005/0119644 A1 | 6/2005 | Koerner | |
| 2005/0131279 A1 | 6/2005 | Boulais et al. | |
| 2005/0182475 A1 | 8/2005 | Jen et al. | |
| 2005/0272975 A1 * | 12/2005 | McWeeney et al. | 600/113 |
| 2005/0273084 A1 | 12/2005 | Hinman et al. | |
| 2005/0273085 A1 | 12/2005 | Hinman et al. | |
| 2006/0041188 A1 | 2/2006 | Dirusso et al. | |
| 2006/0074442 A1 | 4/2006 | Noriega et al. | |
| 2006/0094931 A1 | 5/2006 | Danitz et al. | |
| 2006/0100687 A1 | 5/2006 | Fahey et al. | |
| 2006/0111209 A1 | 5/2006 | Hinman et al. | |
| 2006/0111210 A1 | 5/2006 | Hinman | |
| 2006/0111615 A1 | 5/2006 | Danitz et al. | |
| 2006/0111616 A1 | 5/2006 | Danitz | |
| 2006/0111649 A1 | 5/2006 | Zhou | |
| 2006/0189896 A1 | 8/2006 | Davis et al. | |
| 2006/0241564 A1 | 10/2006 | Corcoran et al. | |

FOREIGN PATENT DOCUMENTS

| | | |
|---|---|---|
| EP | 1 046 406 A2 | 10/2000 |
| EP | 1 174 077 A1 | 1/2002 |
| FR | 2 713 492 | 6/1995 |
| JP | 61-118712 | 6/1986 |
| WO | WO 94/10897 | 5/1994 |
| WO | WO 96/33763 | 10/1996 |
| WO | WO 00/25849 | 5/2000 |
| WO | WO 2005/079683 A1 | 9/2005 |
| WO | WO 2005/094661 A1 | 10/2005 |
| WO | WO 2005/094665 A2 | 10/2005 |
| WO | WO 2006/034008 A2 | 3/2006 |
| WO | WO 2007/112185 A2 | 10/2007 |
| WO | WO 2007/112185 A3 | 10/2007 |

OTHER PUBLICATIONS

L. Farrissey, "Metal Shafts: Design to Meet the Required Performance," Medical Device Technology, Dec. 2004, pp. 1-4.

* cited by examiner

STRUCTURE FOR USE AS PART OF A MEDICAL DEVICE

CROSS-REFERENCE TO RELATED CASES

This application claims priority to, and the benefit of Provisional U.S. patent application Ser. No. 61/023,235, filed Jan. 24, 2008, the entirety of which is incorporated herein by reference.

TECHNICAL FIELD

The present invention generally relates to an articulating structure for use during a medical procedure.

BACKGROUND INFORMATION

Medical devices are commonly used to access remote regions of the body to deliver diagnostic or therapeutic agents to those regions and to perform surgical procedures on those regions. For example, endoscopes may use body airways and canals to access the colon, esophagus, stomach, urethra, bladder, ureter, kidneys, lungs, bronchi, uterus, and other organs. Catheters may use the circulatory system as pathways to access treatment sites near the heart or may use the urinary canal to access urinary regions.

Medical devices are often introduced into the body through a large artery such as those found in the groin or in the neck. The devices are often passed through ever-narrower arteries until they can reach the operative site inside the body. Many such pathways may curve, loop around, and even wind back. In order to navigate the medical device through the pathways to the operative site, the medical device must be flexible to allowing bending, yet have enough column strength to prevent buckling of the medical device as it is pushed. Pull wires incorporated into the medical device can be used to articulate a distal end of the device.

SUMMARY OF THE INVENTION

The present invention generally relates to an articulating structure for use as at least part of a medical device.

In one aspect, the invention features an articulating structure comprising an inner member, a sleeve, a pull wire, and an outer member. The inner member defines at least one channel on the outer surface of the inner member. The at least one channel extends along a length of the inner member. The inner member further defines at least one lumen extending through the inner member. The sleeve is disposed in the at least one channel. The pull wire extends within a lumen of the sleeve. The outer member is disposed over the inner member and defines a lumen through which the inner member extends. This structure is designed to be less expensive and less complex than any known pull wire guide arrangement used in or with articulating structures.

According to one exemplary embodiment of the present invention, an articulating structure for use as at least part of a medical device includes an inner member defining at least one channel on its outer surface that extends along a length of the inner member. The inner member also defines at least one lumen extending through the inner member and can be made of a plastic material such as silicone or PEBAX® (polyether block amide). A sleeve is disposed in the channel. The sleeve can be a plurality of woven strings made from polytetrafluoroethylene or one or more aramid fibers, or the sleeve could be a wound element. The structure includes a pull wire extending within a lumen of the sleeve. The pull wire can be flat or round and made from a material such as stainless steel. The structure also includes an outer member disposed over the inner member and defines a lumen through which the inner member extends. The outer member can be a cut metal tube, a wound element, or flexible plastic.

In another aspect of the invention, the structure further includes a plurality of channels and a plurality of pull wires, and each pull wire is seated in a different one of the channels. The pull wires can have a distal end that is bent to secure it at its distal end of the structure. The structure can also include an outer sheath disposed over the outer member.

BRIEF DESCRIPTION OF THE DRAWINGS

For a more complete understanding of the nature and operation of various embodiments according to the invention, reference is made to the drawings briefly described below and also to the description that follows this brief description of the drawings. The same or similar reference numbers in the drawings generally denote the same or similar elements of the various disclosed embodiments. The drawings are not necessarily to scale, emphasis instead generally being placed on conveying certain concepts and aspects according to the invention.

DESCRIPTION

Figures 1A, 1B:
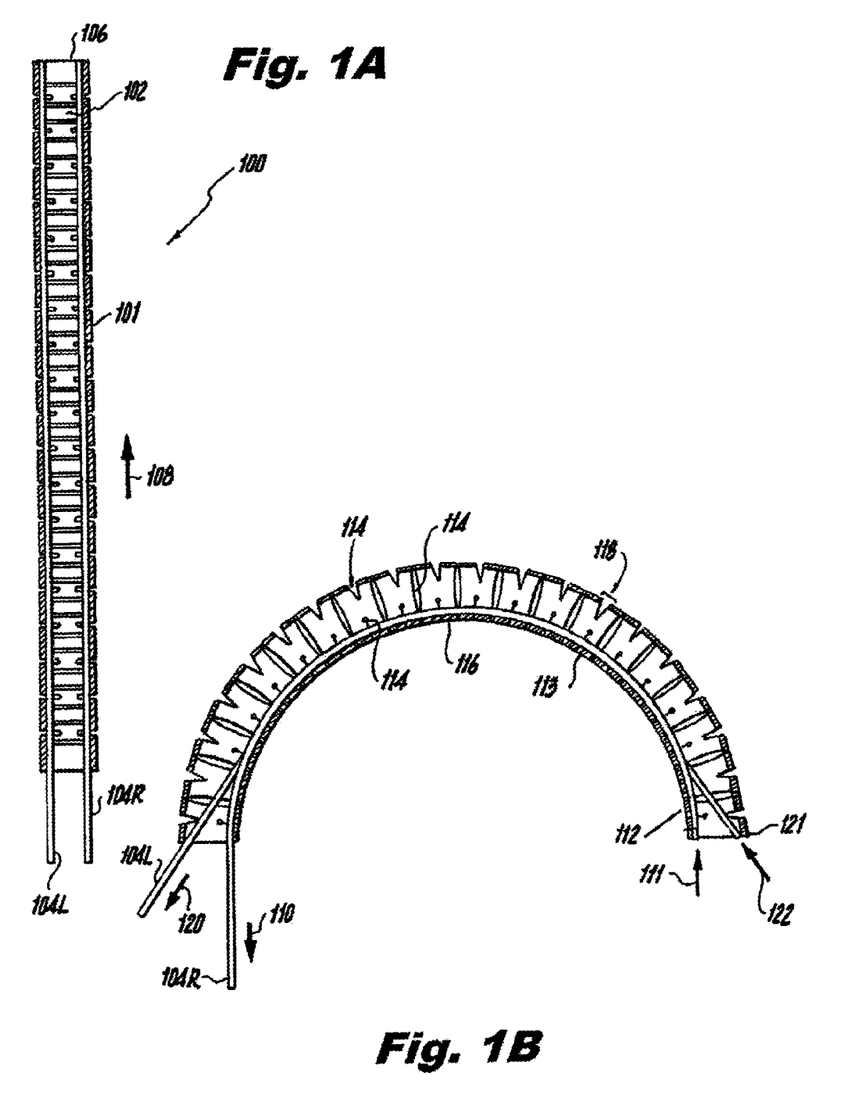
FIG. 1A is a diagram of a tube structure with a left and a right pull wire attached to the distal end of the tube structure, but not attached to the inner surface of the tube structure.
FIG. 1B is a diagram of a tube structure with a left and a right pull wire attached to the distal end of the tube structure and portraying how the tube structure bends when the right pull wire is initially pulled and the left pull wire is subsequently pulled, when neither pull wire is attached to the inner surface of the tube structure.

FIG. 1A shows a tube structure 100 with slots 102 cut into the tube to promote bending and with two pull wires 104L and 104R attached to the distal end 106 of the tube structure 100, but not attached to the inner surface of the tube structure 100. The pull wires 104L and 104R extend longitudinally 108 along the inner surface 101 of the structure 100, on the left side and the right of the structure, respectively. The structure 100 will bend when one of the pull wires is pulled, which applies a force to the distal end of the structure 106 at the attachment point of the pull wire with the tube structure. The direction of bending depends on which pull wire is initially pulled. For example, when the right pull wire 104R is pulled 110, a force 111 is applied in a longitudinal direction on the right side of the distal end 112 of the tube structure 100, causing the structure to collapse 116 at the slot regions 114 along the right side of the structure, and expand 118 at the slot regions 114 along the left side of the structure. In this orientation, the left pull wire 104L shifts from its initial position along the left inner surface, to a position along the right inner surface 113 of the tube structure 100, as shown in FIG. 1B. When the left pull wire 104L is subsequently pulled 120 in this orientation, a force 122 is applied to the left distal end 121 of the tube structure 100, but because the left pull wire is in contact with the right inner surface 113, the force 122 tends to further bend the tube structure to the right (the initial direction) as shown in FIG. 1B. The term proximal and distal require a point of reference. In this application, the point of reference is the perspective of the user. Therefore, the term proximal will always refer to an area closest to the user, whereas distal will always refer to an area away from the user.

Figure 2:
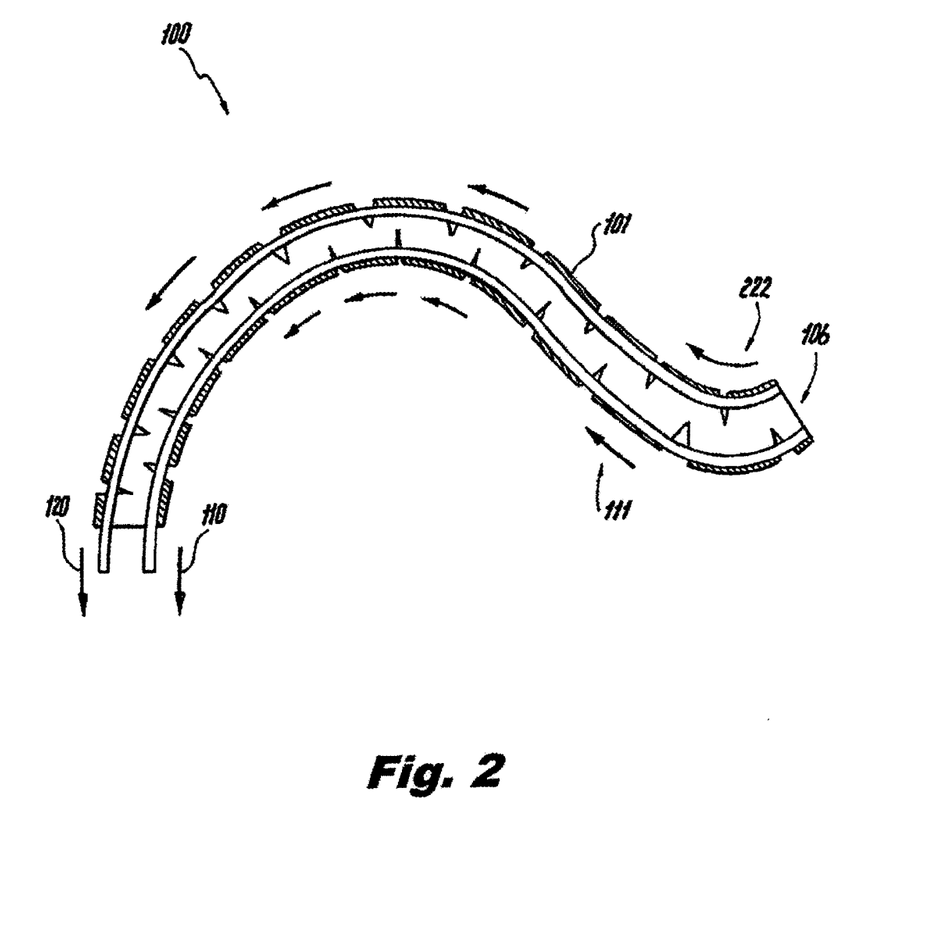
FIG. 2 is a diagram of a tube structure with a left and a right pull wire attached longitudinally along the inner surface of the tube structure as well as at the distal end of the tube structure. The diagram portrays how the tube structure bends when the right pull wire is initially pulled and the left pull wire is subsequently pulled.

FIG. 2 shows the same tube structure but now with each of the pull wires attached longitudinally along the inner surface 101 of the structure 100, in addition to being attached at the distal end 106 of the tube structure 100. The attachment of the pull wires to the inner surface 101 can be continuous along the length of the inner surface 101 or attachment points can be spaced along the inner surface. As described above, when the right pull wire 104R is pulled in the direction of arrow 110, the structure 100 bends to the right as shown. However, because the left pull wire 104L is held in place along the inner surface 101 of the structure 100, when the left pull wire 104L is subsequently pulled in the direction of arrow 120, it applies a force 222 along the left inner surface of the structure and, thus, the structure tends to bend to the left. In this way, the pull wires of FIG. 2 can independently control the direction of bending of the tube structure and thus pull wires have superior control characteristics over the pull wires shown in FIGS. 1A and 1B.

Figures 3A, 3B, 3C:
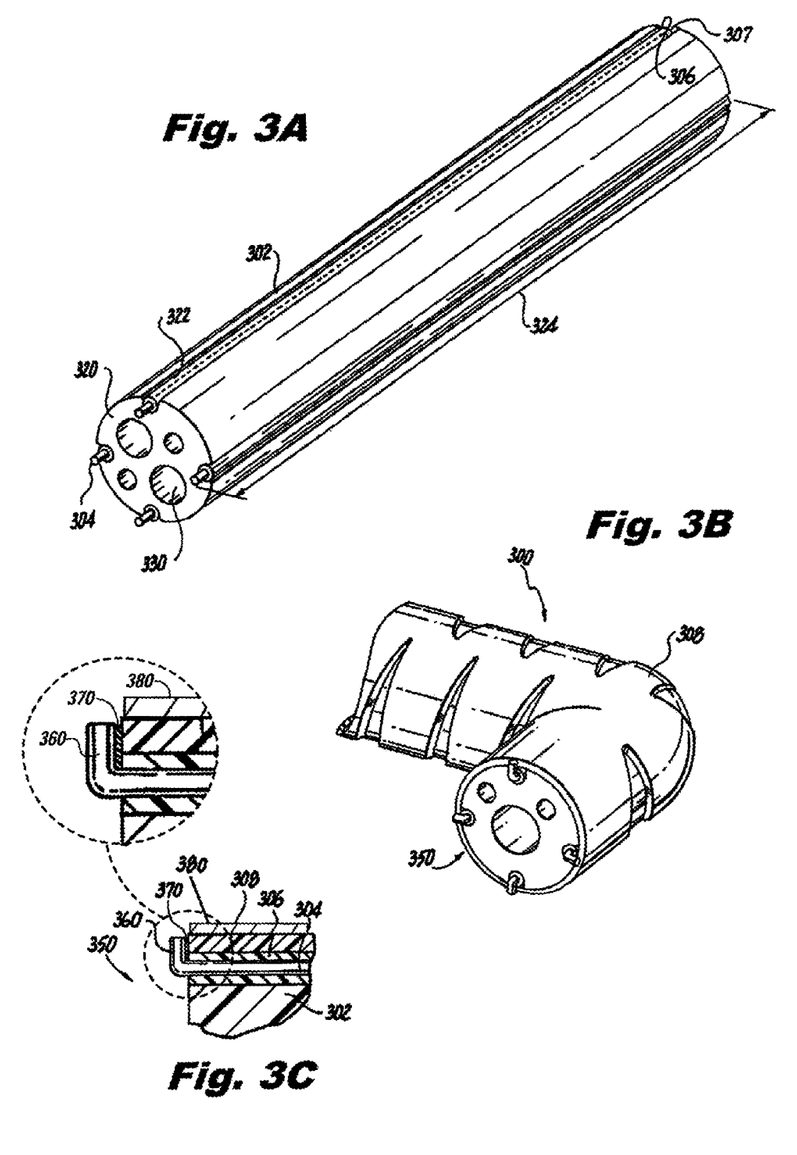
FIG. 3A is a diagram depicting the inner member of the articulating structure with channels, sleeves, and pull wires.
FIG. 3B is a diagram depicting the articulating structure, including the outer member.
FIG. 3C is a diagram depicting an embodiment of the articulating structure including a distal end attaching tip.

In one aspect, the invention is directed to an articulating structure 300 for use as at least part of a medical device comprising an inner member 302, a sleeve 306, a pull wire 304, and an outer member 308, as shown in FIGS. 3A and 3B. The medical device may be an endoscope or a catheter, for example. The structure 300 is designed to hold the pull wires in place and to be less expensive and less complex than any known pull wire guide arrangement used in articulating structures.

The inner member 302 defines at least one channel 322 on its outer surface 320. The at least one channel 322 extends along a length 324 of the inner member 302. The inner member 302 also defines at least one lumen 330 extending through the inner member 302. Medical instruments may be disposed in the at least one lumen 330. Other devices may be disposed in the at least one lumen 330, such as wires for carrying electronic signals from a camera at the distal end of the medical device to an imaging unit.

In one embodiment, the inner member 302 is a very flexible element. It can be formed of plastic, for example, polyethylene, polyvinyl chloride (PVC), a polyether block amide such as PEBAX® (a thermoplastic elastomer that retains its physical properties over a wide temperature range of about −40 to +80 degrees Celsius) or the like, silicone, co-polymers, and other polymers. And, it can be created using an extrusion process or a molding process, for example.

The sleeve 306 is disposed in one of the channels 322. The sleeve 306 must be strong enough to withstand interaction with the pull wire 304, yet be flexible enough to accommodate stretching and compression of the structure 300. The sleeve 306 must also prevent the pull wire 304 from damaging the flexible inner member 302.

In one embodiment, the sleeve 306 can be comprised of a plurality of woven strings. In a further embodiment, the woven strings can be made of a high strength polymer such as KEVLAR® (poly-paraphenylene terephthalamide) (an aramid fiber or yarn) or they can be made of a polytetrafluoroethylene, such as TEFLON®. In still another embodiment, the sleeve 306 is a wound element 400.

Figure 4A:
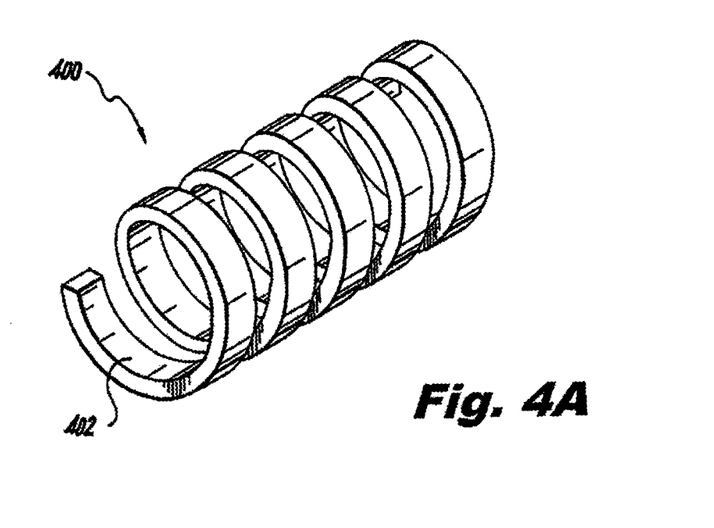
FIG. 4A is a diagram depicting an embodiment of the articulating structure, wherein the sleeve is a wound flat wire element.
Figure 4B:
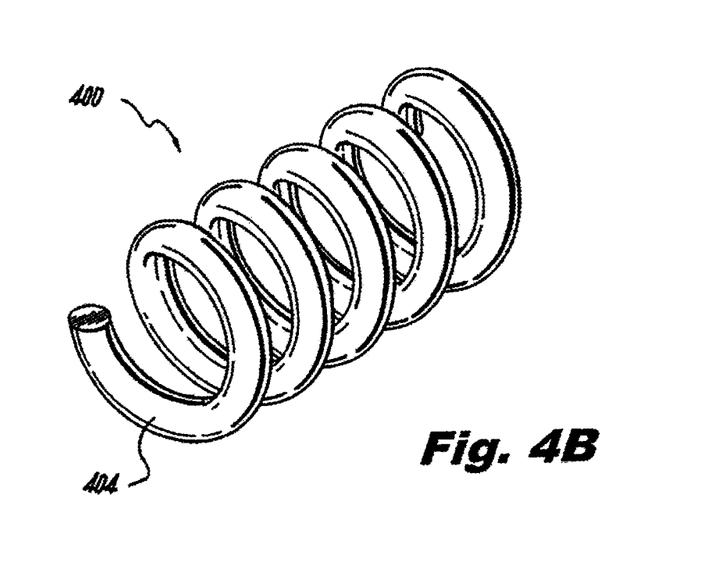
FIG. 4B is a diagram depicting an embodiment of the articulating structure, wherein the sleeve is a wound round, oval, or elliptical wire element.

In one embodiment of the sleeve, the element is a flat wire 402 as shown in FIG. 4A. In another embodiment, the element is a round wire 404 as shown in FIG. 4B, or it could be oval or elliptical in cross section, for example.

The pull wire 304 extends within a lumen 307 of the sleeve 306. The pull wire is held in place along the outer surface 320 of the inner member 302 by the sleeve 306 disposed in the channel 322. Pulling on the pull wire 304 tends to bend the structure 300 as shown in FIG. 2 and explained above for the tube structure 100 and pull wires 104L and 104R. Because the articulating structure 300 of the invention includes pull wires 304 held in place longitudinally along the outer surface 320 of the inner member 302, each pull wire 304 can maintain independent control over the direction of bending of the articulating structure 300. Thus, as shown in FIG. 2, initially pulling a right pull wire of the structure 300 will tend to bend the structure 300 to the right, and subsequent pulling a left pull wire of the structure 300 will tend to bend the structure to the left.

In one embodiment, the pull wire 304 may be comprised of stainless steel. The pull wire 304 may be fastened to the distal end 350 of the structure 300 by securing it to the outer member 308 using solder or epoxy 370. In one embodiment, the pull wire 304 has a bent distal end or tip 360 to attach and secure that distal end of the pull wire 304 to the distal end 350 of the structure 300.

Figure 5A:
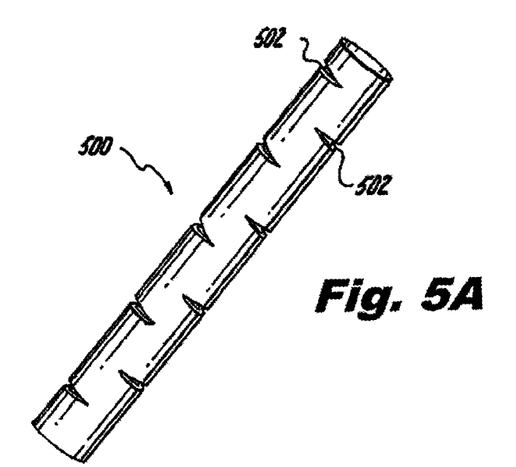
FIG. 5A is a diagram depicting an embodiment of the outer member, wherein the outer member is a cut metal tube.
Figures 5B, 5C:
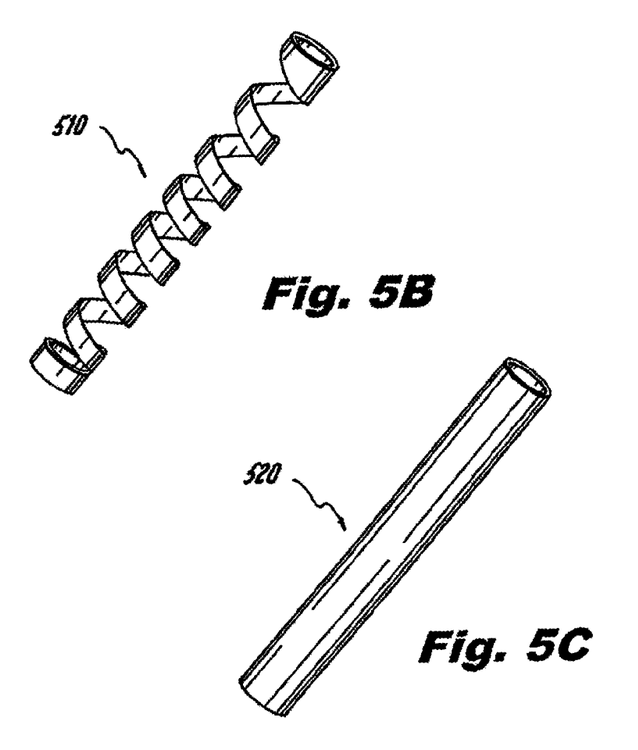
FIG. 5B is a diagram depicting an embodiment of the outer member, wherein the outer member is a wound element.
FIG. 5C is a diagram depicting an embodiment of the outer member, wherein the outer member is a flexible plastic tube.
Figure 6A:
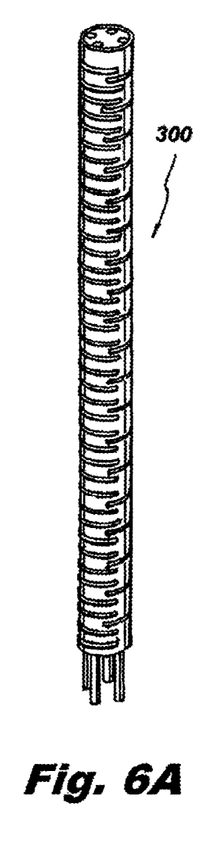
FIG. 6A is a diagram depicting an embodiment of the articulating structure, wherein the outer member is a cut metal tube.
Figure 6B:
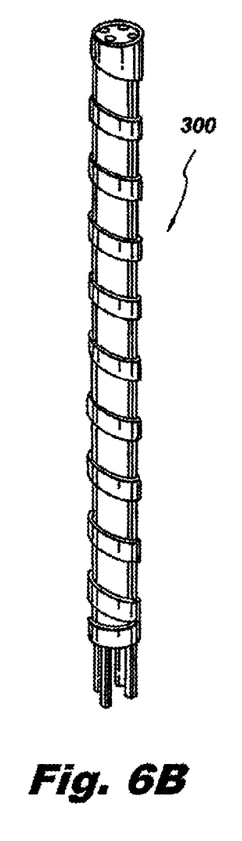
FIG. 6B is a diagram depicting an embodiment of the articulating structure, wherein the outer member is a wound element.
Figure 6C:
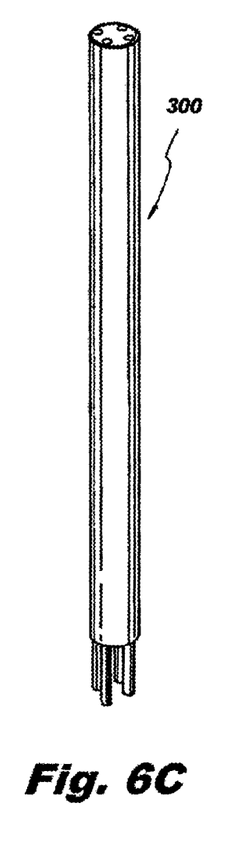
FIG. 6C is a diagram depicting an embodiment of the articulating structure, wherein the outer member is a flexible plastic tube.

The outer member 308 must be flexible enough to permit traversal of the structure 300 through body pathways to the operative site, yet provide enough column strength to prevent buckling of the structure 300 it is pushed and controlled with the pull wires 304. In one embodiment shown in FIG. 5A, the outer member is a cut metal tube 500. For example, the cut metal tube can be comprised of a series of opposing cut slots 502 extending longitudinally along a length of the structure. The slots promote bending of the structure by collapsing or expanding the outer member at the slot regions in response to a force applied to the pull wire. In another embodiment shown in FIG. 5B, the outer member is a would element 510. In still another embodiment shown in FIG. 5C, the outer member is a flexible plastic 520. FIGS. 6A, 6B, and 6C show the articulating structure wherein the outer member is a cut metal tube 500, a wound element 510, and a flexible plastic 520, respectively.

In one embodiment, the structure 300 further comprises an outer sheath 380 disposed over the outer member 308. The outer sheath 380 can be made of, or alternatively can have a coating of, a hydrophobic or lubricious material that makes it "slippery" on its surface(s) such as, for example, TEFLON®. (polytetrafluoroethylene) (a waxy, opaque material), or the like. The outer sheath 380 can be heat shrunk over the outer member 308 into tight engagement with the outer member 308 and the overall structure 300. The outer sheath 380 can be secured to the outer member 308 with an adhesive applied on the outer surface of the outer member 308 or at various affixation points on the outer surface of the outer member 308. The adhesive can be a thermo-plastic adhesive that softens at the temperature necessary to heat shrink the outer sheath 380.

FIGS. 3A and 3B show an embodiment of the articulating structure 300 with four channels 322, four sleeves 306 disposed in the channels, and four pull wires 304 extending through the sleeve lumens 307, however, any number of corresponding channels, sleeves, and pull wires may be used, for example, 1, 2, 3, 4, etc.

The articulating structure 300 for use as at least part of a medical device can be manufactured any number of ways. For example, the inner member 302 can be extruded or molded with channels formed along the outer surface 320 of the inner member to hold the sleeves 306. The inner member can be inserted into the outer member 308. The pull wires 304 can be inserted into the protective sleeves 306. The sleeve-pull wire assembly can be inserted into channels of the inner member 302 and secured to the distal end of the articulating structure.

Alternatively, the protective sleeve and pull wires can be preloaded into the outer member along the inner surface of the outer member. The inner member can be injected into the outer member and allowed to dry, thereby holding the sleeves in place along the outer surface of the injected inner member.

Articulating structures according to the invention have a variety of advantages over known structures. The articulating structure is relatively inexpensive to manufacture compared to other structures comprised of complex assemblies for securing pull wires and for controlling articulating tips with the pull wires. The articulating structure can include any number of pull wires, depending on the needs of the medical application, and each pull wire can independently control the direction of movement of the articulating structure, thus making the structure highly adaptive to tortuous body pathways.

While certain embodiments according to the invention are shown and described, other embodiments are within the scope of this disclosure and are considered to be part hereof. The invention is not to be limited just to certain embodiments shown and/or described.

What is claimed is:

1. A medical device with an articulating structure, the structure comprising:
    an inner member having an outer surface defining a channel on the outer surface, the channel extending along a length of the inner member, the inner member also defining a lumen extending through the inner member;
    a sleeve disposed in the channel;
    an outer member disposed over the inner member, the outer member defining a lumen through which the inner member extends; and
    a pull-wire extending within a lumen of the sleeve,
    wherein a portion of the pull-wire extends distally of a distal-most end face of the outer member, the portion of the pull-wire extending distally of the distal-most end face of the outer member including a bent portion,
    wherein the bent portion is bent radially outwardly and is directly secured to the distal-most end face of the outer member via at least one of solder and epoxy, and
    wherein the bent portion of the pull-wire is distal of both the inner and outer members.

2. The medical device of claim 1 wherein the inner member comprises plastic.

3. The medical device of claim 2 wherein the plastic comprises silicone or a polyether block amide.

4. The medical device of claim 1 wherein the sleeve comprises a plurality of woven strings.

5. The medical device of claim 4 wherein the woven strings are made of polytetrafluoroethylene or one or more aramid fibers.

6. The medical device of claim 1 wherein the sleeve comprises a wound element.

7. The medical device of claim 6 wherein the wound element comprises a flat wire or a round wire.

8. The medical device of claim 1 wherein the pull-wire comprises stainless steel.

9. The medical device of claim 1 wherein the outer member comprises a cut metal tube.

10. The medical device of claim 1 wherein the outer member comprises a wound element.

11. The medical device of claim 1 wherein the outer member comprises a flexible plastic.

12. The medical device of claim 1 further comprising a plurality of channels and a plurality of pull-wires, wherein each pull-wire of the plurality of pull-wires is seated in a different one of the plurality of channels.

13. The medical device of claim 12 comprising at least four channels and at least four pull-wires.

14. The medical device of claim 1 further comprising an outer sheath disposed over the outer member.

15. The medical device of claim 1 wherein a distal-most end face of the inner member is coplanar with the distal-most end face of the outer member.

16. The medical device of claim 1 wherein the outer member comprises a first material and the inner member comprises a second material that is more flexible than the first material.

17. The medical device of claim 1 wherein the lumen defined by the outer member has a longitudinal axis and the bent portion is bent outwardly in a direction transverse to the longitudinal axis.

18. The medical device of claim 1 wherein the bent portion is directly secured to the distal-most end face of the outer member so as to transfer a force from the pull-wire to the outer member.

19. A medical device with an articulating structure, the structure comprising:
    an inner member having an outer surface defining a channel on the outer surface, the channel extending along a length of the inner member, the inner member also defining a lumen extending through the inner member;
    a sleeve disposed in the channel;

an outer member disposed over the inner member, the outer member defining a lumen through which the inner member extends; and a pull-wire extending within a lumen of the sleeve, wherein a portion of the pull-wire extends distally of a distal-most end face of the outer member, the portion of the pull-wire extending distally of the distal-most end face of the outer member including a tip with a proximal-facing surface, wherein the proximal-facing surface of the tip extends radially outwardly and is directly secured to the distal-most end face of the outer member, and wherein the tip of the pull-wire is distal of both the inner and outer members.

20. The medical device of claim 19 wherein the proximal-facing surface of the tip is directly secured to the distal-most end face of the outer member so as to transfer a force from the pull-wire to the outer member.

* * * * *